United States Patent [19]

Stühler et al.

[11] Patent Number: 4,948,535

[45] Date of Patent: Aug. 14, 1990

[54] PROCESS FOR THE SULFATION OF PARTIAL ESTERS OF ALIPHATIC POLYHYDRIC ALCOHOLS

[75] Inventors: Herbert Stühler, Burgkirchen; Klaus Dullinger, Neuötting, both of Fed. Rep. of Germany

[73] Assignee: Hoechst Aktiengesellschaft, Frankfurt am Main, Fed. Rep. of Germany

[21] Appl. No.: 467,274

[22] Filed: Jan. 23, 1990

Related U.S. Application Data

[63] Continuation of Ser. No. 119,859, Nov. 12, 1987, abandoned.

[30] Foreign Application Priority Data

Nov. 13, 1986 [DE] Fed. Rep. of Germany ....... 3638742
Jul. 17, 1987 [DE] Fed. Rep. of Germany ....... 3723702

[51] Int. Cl.$^5$ .................. C07C 303/00; C07C 303/06
[52] U.S. Cl. .................................... 260/400; 260/403
[58] Field of Search .......................................... 260/400

[56] References Cited

U.S. PATENT DOCUMENTS

| | | |
|---|---|---|
| 2,014,502 | 9/1935 | Marx et al. |
| 2,087,506 | 7/1937 | De Groote ........................... 260/400 |
| 2,180,342 | 11/1939 | Auer .................................... 260/400 |
| 2,201,535 | 5/1940 | Harris .................................. 260/400 |
| 2,212,521 | 8/1940 | Harris .................................. 260/400 |
| 2,242,979 | 5/1941 | Muncie . |
| 2,268,443 | 12/1941 | Crowder ............................. 260/400 |
| 2,280,118 | 4/1942 | Dombrow ........................... 260/400 |
| 2,285,773 | 6/1942 | Harris .................................. 260/400 |
| 2,626,264 | 1/1953 | Brod et al. .......................... 260/400 |
| 2,634,287 | 4/1953 | Fincke . |
| 2,868,812 | 1/1959 | Gray . |

FOREIGN PATENT DOCUMENTS

273375 2/1951 Switzerland .
364107 12/1931 United Kingdom .

OTHER PUBLICATIONS

Biswas, A. K. et al, J. Amer. Oil Chem. Soc. 37, 171–172 (1960).

*Primary Examiner*—Patrick P. Garvin
*Assistant Examiner*—E. D. Irzinski

[57] ABSTRACT

A process for the sulfation of primary free OH groups of partial esters of aliphatic polyhydric alcohols with $SO_3$ is described. As solvent, use is made of at least one compound which has a boiling point of 40° to 200° C. at a pressure of 98 kPa, is liquid under the chosen reaction conditions and, in addition to at least one trivalent nitrogen atom, which is linked exclusively to carbon atoms, contains only carbon, hydrogen and optionally ether oxygen atoms. The sulfated partial esters and also their alkali of alkaline earth salts are obtained with a good color and good yield and without the formation of large quantities of salts which pollute the waste water. They may be used, for example, for detergent base materials, synthetic soaps and flotation agents.

10 Claims, No Drawings

PROCESS FOR THE SULFATION OF PARTIAL ESTERS OF ALIPHATIC POLYHYDRIC ALCOHOLS

This is a continuation application of U.S. patent application Ser. No. 199,859, filed on Nov. 12, 1987, now abandoned.

The invention relates to a process for the sulfation of partial esters of aliphatic polyhydric alcohols with $SO_3$ in the presence of a solvent.

Sulfated partial esters of polyhydric aliphatic alcohols, for example, sulfates of fatty acid monoglycerol esters, are valuable surfactants which are used as detergent base materials, soaps or flotation agents. Various processes are known for preparing them:

According to U.S. Pat. No. 2,242,979, a sulfonating agent, for example sulfuric acid, is mixed with a polyhydric alcohol at 30° C. and subsequently allowed to react with fatty acid or fats or oils while being heated, and then neutralized. The excess of sulfuric acid should be so large that at the end of the reaction a 99.3% acid by weight is still present.

According to U.S. Pat. No. 2,014,502 a mixture of saturated fatty acids, or of fatty acid glycerides and polyhydric alcohols in a mixture ratio which permits the formation of free hydroxyl groups in the fatty acid esters containing alcohol radicals is sulfonated with a large excess of concentrated to anhydrous sulfuric acid and then neutralized with alkali hydroxide solution or nitrogen base.

According to Swiss patent No. 273,375, molar quantities of glycerol, coconut oil and tallow are reacted in the presence of a large excess of fuming sulfuric acid (containing, for example, approximately 20% $SO_3$) poured onto ice and neutralized with aqueous sodium hydroxide solution.

According to U.S. Pat. No. 2,868,812, 1 mol of an essentially saturated fat triglyceride, 2 mol of glycerol trisulfuric acid and 4.0 to 4.8 mol of sulfuric acid monohydrate are reacted at 30° to 65° C. and then neutralized with sodium hydroxide solution.

According to U.S. Pat. No. 2,634,287, for example, 1 mol of glycerol monolaurate is reacted in liquid $SO_2$ at at least 20° C. with 1 mol of $SO_3$ in liquid $SO_2$, the $SO_2$ evaporated off and the reaction product neutralized with sodium hydroxide solution.

According to British Patent No. 364,107, Example 3, glycerol monolaurate is reacted with an excess of concentrated sulfuric acid at 60° C., poured onto ice and extracted with butyl acetate. This extract is neutralized with aqueous sodium carbonate solution and separated from the butyl acetate.

According to K. Engel and W. Ruback, "Fette, Seifen, Anstrichmittel", 88 (1986), pages 21 and 22, fatty acid monoglycol esters are reacted with chlorosulfonic acid, temperatures of −20° to 0° C. proving to be beneficial. After neutralization, 30% aqueous sodium salt solutions of the fatty acid glycol ester sulfates are obtained.

Finally, according to A. K. Biswas and B. K. Nukherji, The Journal of the American Oil Chemists Society 37 (1960), page 172, right-hand column, a considerable excess of pyridine sulfur trioxide complex is added to an unsaturated fatty acid monoglyceride at 10° C., the reaction mixture is dissolved in hot n-butanol and neutralized with hot sodium hydroxide solution.

The processes based on the prior art have at least one of the following disadvantages:
  formation of considerable quantities of sodium sulfate which pollute the waste water;
  formation of HCl, the disposal of which incurs costs; working under pressure with aggressive media is necessary; the working up to the dry substance is energy-intensive since considerable quantities of water have to be evaporated;
  a mixture of organic solvents is produced which have to be separated by distillation before being reused; a special reaction step is necessary to produce the sulfating agent.

A process has now been found which does not have the disadvantages described above and which produces light-colored products with good yields. The new process for the sulfation primary, free OH groups of partial esters of aliphatic polyhydric alcohols with $SO_3$ in the presence of a solvent is a process wherein at least one compound is used as solvent which has a boiling point of 40° to 200° C. at a pressure of 98 kPa, is liquid under the chosen reaction conditions and in addition to at least one trivalent nitrogen atom, which is linked exclusively to carbon atoms, contains only carbon, hydrogen and optionally ether oxygen atoms.

Suitable aliphatic polyhydric alcohols with several primary free OH groups are, for example, ethylene glycol, glycerol, diglycerol, polyglycerols produced by eliminating water from glycerol, pentaerythritol and sugar alcohols such as mannitol or sorbitol. The ethylene oxide reaction products of these alcohols may also be used. Preferably, at least one carboxylic acid monoester of glycerol, diglycerol, ethylene glycol or diethylene glycol is used as partial ester.

Suitable esterification components of the aliphatic polyhydric alcohols are aliphatic carboxylic acids containing 1 to 25 carbon atoms or arylaliphatic carboxylic acids containing 7 to 16 carbon atoms, particularly monocarboxylic acids with terminal COOH groups, such as, for example, acetic acid, butanoic, octanoic, lauric, palmitic and stearic acid. These acids may contain double bonds in the carbon chain, such as, for example, oleic, linoleic, linolenic, brassidic or erucic acid. The aliphatic carboxylic acids may contain secondary hydroxyl groups, such as, for example, hydroxystearic acid or ricinoleic acid. Preferably, use is made of partial esters of aliphatic polyhydric alcohols with aliphatic monocarboxylic acids which contain 8 to 22 carbon atoms and may contain double bonds or secondary hydroxyl groups respectively. Mixtures of such partial esters may also be used provided they still contain free primary hydroxyl groups, for example, a mixture of glycerol monocarboxylic acid ester and glycerol dicarboxylic acid ester.

The reaction with $SO_3$ takes place according to the invention in the presence of a solvent which has a boiling point of 40° to 200° C. at a pressure of 98 kPa, is liquid under the chosen reaction conditions and in addition to at least one trivalent nitrogen atom, which is linked exclusively to carbon atoms, contains only carbon, hydrogen and optionally ether oxygen atoms. Examples of suitable compounds are: triethylamine; diisopropylethylamine; triisopropylamine, tri-n-propylamine; triisobutylamine; methyldiethylamine; N,N-dimethylcyclohexylamine; N,N-dimethylaniline; pyrimidine; pyridine; N-methylpiperidine; N-methylpyrrole; 2-methylpyrazine; 1-methylimidazole; N-methylpyrrolidine; N-methyl- and N-ethylmorpholine. Preferably, use is made of compounds in which a nitrogen atom is linked to 3 carbon atoms.

Under the chosen reaction conditions, the nitrogen-containing compounds used as solvent should be liquid. Since the reaction of the partial ester with the $SO_3$ advantageously takes place at 0° to 60° C., nitrogen-containing compounds may be used as solvents whose boiling point is 10° C. or above at 98 kPa. The boiling point is limited in the upward direction at the said pressure by economic considerations and by the fact that compounds with a high boiling point are, as a rule, no longer liquid under the chosen reaction conditions. Advantageously, a nitrogen-containing solvent is used which has a boiling point of 40° to 200° C., in particular of 60 to 150° C., at a pressure of 98 kPa. The $SO_3$ can be used in solid or liquid form, advantageously it is used in gaseous form diluted with an inert gas, for example, nitrogen, air or argon. Good results are obtained if the gas mixture contains 1 to 30% by volume and in particular 2 to 10% by volume of $SO_3$. Such a gas mixture may, for example, be produced by passing a stream of nitrogen over optionally heated $SO_3$ or fuming sulfuric acid. The partial esters of aliphatic polyhydric alcohols dissolved in the nitrogen-containing solvent can be brought into contact with the $SO_3$-containing gas stream in various ways, for example by passing the latter into or over the liquid, which is expediently set in motion by stirring, or by allowing a liquid film to trickle down which is passed either in cocurrent with or countercurrent to the $SO_3$-containing gas mixture.

0.9 to 1.2 mol of $SO_3$ are advantageously used per 1 mol of primary free OH groups of the partial ester of the aliphatic polyhydric alcohol. Below 0.9 mol of $SO_3$, undesirably low sulfation products are in general obtained, about 1.2 mol of $SO_3$ undesirable further reactions often occur, and also the salt pollution due to the process becomes unnecessarily high after the neutralization.

The temperature during the reaction of the partial ester of the aliphatic polyhydric alcohol with $SO_3$ may vary in wide limits. Advantageously, it is carried out at 0° to 60° C., in particular at 10° to 40° C. Excessively high temperatures favor undesirable side reactions, and excessively low temperatures unnecessarily increase the duration of the reaction. The reaction according to the invention can be carried out at a different pressure, but because of the low apparatus cost, normal atmospheric pressure is in general preferred.

The progress of the sulfation is expediently followed by analytical methods, for example by titration of a sample, which has previously been freed of solvent by evaporation, with alkali hydroxide solution. When the desired quantity of $SO_3$ has been absorbed by the reaction mixture, the supply of $SO_3$ is terminated and a post reaction time of about 0.5 to 3 h may additionally follow, during which the reaction mixture continues to be kept in motion while the reaction temperature is maintained or the temperature is increased to up to 120° C., optionally under pressure. The reaction duration depends on the chosen temperature, the concentration of the $SO_3$, the nature of the partial ester of the aliphatic polyhydric alcohol and the manner in which the reactants are brought into contact. In general, times of 0.5 to 20 h, preferably 3 to 10 h, are sufficient.

After stopping the addition of $SO_3$ and optionally after a post reaction time, the product may be separated from the solvent, for example, by distilling off, and the amine salt of the sulfated partial ester of the aliphatic polyhydric alcohol then results which may already be used as such. In many cases, however, the alkali or alkaline earth salt of the sulfated ester is desirable. This is advantageously prepared by a process wherein, after stopping the addition of $SO_3$ and optionally after a post reaction time, an alkali hydroxide or alkaline earth hydroxide is added to the reaction mixture and the solvent is then distilled off. Because of the easy procurability, potassium or calcium hydroxide, and in particular sodium hydroxide, are preferred. Good results are obtained if 1 to 1.4 equivalents of the alkali hydroxide or alkaline earth hydroxide are used per 1 mol of $SO_3$ employed. During the separation of the nitrogen-containing solvent, expediently by distillation, the pressure is advantageously adjusted so that the bottom temperature is 30° to 90° C. At higher temperatures the risk of the formation of impurities increases, and preferably, a bottom temperature in the range 40° to 70° C. is employed.

After removal of water, the nitrogen-containing solvent separated from the reaction product is advantageously reused for the reaction according to the invention. In general, so much solvent is used that at least one third, preferably the entire partial ester of the aliphatic polyhydric alcohol goes into solution at the chosen reaction temperature. In order to avoid introducing larger quantities of water into the process, the alkali hydroxide may be dissolved in the nitrogen-containing solvent or used diluted with the latter for the neutralization. Instead of the alkali hydroxide or alkaline earth hydroxide, a quaternary ammonium hydroxide may also be used.

After the treatment with alkali hydroxide, alkaline earth hydroxide or quaternary ammonium hydroxide and separating off the nitrogen-containing solvent, for example by distillation, the alkali, alkaline earth or quaternary ammonium salt of the sulfated partial ester of the aliphatic polyhydric alcohol is left behind as residue as a light-colored to white substance of purity which is sufficient for most applications. If necesssary, further purification operations which are known per se may follow.

The process according to the invention makes it possible to prepare light-colored substances with good surfactant properties which contain comparatively small amounts of foreign salts. Normal pressure can substantially be employed, and only the distilling off of the solvent may sometimes require reduced pressure.

As already mentioned in the introduction, the substances prepared according to the new process are suitable, for example, as detergent base materials, for synthetic soaps or as flotation agents.

The examples below are intended to explain the invention in more detail:

EXAMPLE 1

50 g of a product which contains 91% by weight of glycerol monolaurate (which is 0.165 mol of glycerol monolaurate) in addition to more highly esterified products are dissolved in 300 cm³ of triethylamine at 22° C. while stirring in a vessel with a capacity of 1 dm³ which is provided with thermometer, stirrer, condenser and gas inlet tube. While stirring is continued, a gas mixture which contains 2.3% by volume of $SO_3$ in addition to nitrogen is now fed in through the gas inlet tube whose orifice terminates above the surface of the liquid within 8 h. 13.5 g of $SO_3$ = 0.168 mol were absorbed, and consequently 1.02 mol of $SO_3$ were used per 1 mol of partial ester. The temperature rises to 25° C. and is maintained at this level. During the reaction, small samples are removed, the solvent is evaporated off and the acid number in the residue determined by titration with aqueous sodium hydroxide solution. The introduction of the $SO_3$-containing gas mixture is stopped when an acid number of 145 mg KOH/g of substance is reached, then stirring is continued for a further 1 h without gas being fed in. After evaporating off the solvent, a sample of the reaction mixture contains 90% by weight of the triethylamine salt of the sulfated glycerol monolaurate as determined by two-phase titration by the Epton method, and in addition 2.1% by weight of $H_2SO_4$ determined as sulfate. 28.3 g of a 30% by weight sodium hydroxide solution in water, which was diluted with 50 cm$^3$ of triethylamine, was then slowly added dropwise to the reaction mixture at 22° C. while stirring. The triethylamine is then distilled off at a bottom temperature of 60° C. and a reduced pressure down to a final value of 2 kPa. The sodium salt of the sulfated glycerol monolaurate is obtained as residue as a white odorless powder. According to analysis, it contains 90% by weight sodium salt of the sulfated product and 3.4% by weight of sodium sulfate.

EXAMPLE 2

The procedure is as described in Example 1, but 70 g of a product which contains 90% by weight of glycerol monostearate (0.175 mol) are dissolved in 235 g of triethylamine in the reaction vessel. A gas mixture which contains 2.3% by volume of $SO_3$ in addition to nitrogen is then fed into the reaction vessel for several hours at 26° C. while the liquid is being stirred until an acid number of 120 mg KOH/g of substance is reached, and stirring is then continued for a further 40 min. In total, 14.3 g of $SO_3$ = 0.1785 mol are fed in, which is 1.02 mol of $SO_3$ per mol of glycerol monostearate. After evaporating off the solvent, the reaction mixture contains 90% by weight of the triethylamine salt of the sulfated glycerol monostearate as determined by two-phase titration by the Epton method, in addition to 2.3% by weight of sulfuric acid determined as sulfate. 32 g of a 30% by weight sodium hydroxide solution in water which was diluted with 50 cm$^3$ of triethylamine are then slowly added dropwise at 22° C. while stirring as described in Example 1. This is 1.34 equivalents of NaOH per mol of $SO_3$. The triethylamine is then distilled off at a bottom temperature of 60° C. and reduced pressure down to 2kPa. The sodium salt of the sulfated glycerol monostearate is obtained as a white odorless powder, and according to analysis, this contains 90% by weight of sodium salt of the sulfated product in addition to 3.6% sodium sulfate.

EXAMPLE 3

The procedure is again as described in Example 1. 100 g of a product which contains 75% by weight of glycerol monolaurate (remainder: more highly esterified products), which is 0.273 mol, are dissolved in 242 g of triethylamine at 22° C. while stirring and then gasified for several hours at 25° C. with a gas mixture which contains 2.3% by volume of $SO_3$ in addition to nitrogen until an acid number of 130 mg KOH/g of substance is determined in the reaction mixture. In total, 23.3 g, which is 0.291 mol of $SO_3$ is fed in as gas, which is 1.06 mol of $SO_3$ per mol of partial ester. Stirring is then continued for a further 60 minutes without gas being fed in. The reaction mixture then contains 75% by weight of the triethylamine salt of the sulfated glycerol monolaurate as determined by two-phase titration by the Epton method, in addition to 2.5% by weight of sulfuric acid determined as sulfate. Analogously to Example 1, 47 g of a 30% by weight sodium hydroxide solution in water, which was diluted with 50 ml of triethylamine are slowly added dropwise at 22° C. to this reaction mixture while stirring. This is 0.352 mol of NaOH, or 1.21 mol of NaOH per mol of $SO_3$. After the neutralization has been stopped, the triethylamine is distilled off at a bottom temperature of 60° under a reduced pressure down to 2 kPa. The sodium salt of the sulfated glycerol monolaurate is again obtained as a white odorless powder. After analysis, the residue contains 70% by weight of the sodium salt of the sulfated product, in addition to 4.3% by weight of sodium sulfate.

EXAMPLE 4

The procedure is as described in Example 1, but 30 g of a product which contains 91% by weight of glycerol monolaurate (which is 0.0993 mol of glycerol monolaurate) in addition to more highly esterified products are dissolved in 250 cm$^3$ of N-methylmorpholine at 21° C. in the reaction vessel while stirring. Then, while stirring is continued, a gas mixture which contains 6% by volume of $SO_3$ in addition to nitrogen is passed within 3.5 h over the surface of the solution, the temperature of the latter being held at 21° C. 8.6 g of $SO_3$ (=0.1074 mol) is absorbed by the solution, which is 1.08 mol of $SO_3$ per 1 mol of glycerol partial ester. After the feeding in of $SO_3$ has been stopped, the reaction mixture is heated for 1 h at 40° C. while stirring. After evaporating off the solvent, a sample of the reaction mixture contains 83% by weight of the N-methylmorpholine salt of the sulfated glycerol monolaurate (determined by two-phase titration by the Epton method) and has an acid number of 212 mg KOH/g. 15.7 g of a 30% by weight aqueous sodium hydroxide solution which was diluted with 30 cm$^3$ of N-methylmorpholine is now added to the reaction mixture and working up is then carried out as described in Example 1. A white odorless powder is obtained.

EXAMPLE 5

The procedure is analogous to Example 1. 50 g of a pentaerythritol ester in which 3 OH groups are esterified with tallow fatty acid (a mixture of straight-chain alkyl monocarboxylic acids with the following carbon chain length distribution: $C_{12}$=1% by weight; $C_{14}$=3% by weight; $C_{16}$=31% by weight; $C_{18}$=65% by weight) (=0.0556 mol) are dissolved in 200 cm$^3$ of ethyldiisopropylamine in the reaction vessel and a gas containing 9.1% by volume of $SO_3$ in addition to nitrogen is passed over the surface of the solution for 52 minutes with the temperature held constant at 25° C. while stirring. 4.79 g of $SO_3$ (=0.0598 mol) are absored by the solution, which is 1.07 mol of $SO_3$ per 1 mol of pentaerythritol ester. After the feeding in of $SO_3$ has been stopped, the reaction mixture is heated for 1 h at 100° C. while stirring. After evaporating off the solvent, a sample of the reaction mixture contains 88.9% by weight of the ethyldiisopropylamine salt of the sulfated pentaerythritol ester (determined by the Epton method) and it furthermore contains 3.4% by weight of sulfate ions and has an acid number of 96 mg KOH/g. 8.8 g of a 30% by weight aqueous sodium hydroxide solution which was diluted with 10 cm$^3$ of ethyldiisopropylamine are then added to the reaction mixture and working up is then carried out as described in Example 1. A beige-colored odorless cohesive crystalline mass is obtained.

EXAMPLE 6

The procedure is analogous to Example 1. 50 g of a technical mixture which, according to gas chromatographic analysis contains 17% by weight of diglycerol, 34% by weight of diglycerol monolaurate, 28% by weight of diglycerol dilaurate, 11% by weight of diglycerol trilaurate and 10% by weight of a remainder consisting of glycerol, glycerol mono-, di- and trilaurate, are dissolved in 250 cm$^3$ tri-n-propylamine in the reaction vessel. The technical ester-containing mixture used has an OH number of 432 mg KOH/g and on the basis of NMR spectroscopic analysis, the mixture contains 37.5% primary OH groups and 62.5% secondary OH groups (percentages in each case referred to the total number of OH groups). From this it follows that, of the total OH number, 162 mg KOH/g are ascribable to primary OH groups and 270 mg KOH/g to secondary OH groups.

A gas containing 4.8% by volume of $SO_3$ in addition to nitrogen is fed into the solution of the mixture for 4.5 h at a temperature held constant at 25° C. while stirring. 13.6 g of $SO_3$ (=0.17 mol) are absorbed by the solution, which is 1.18 mol of $SO_3$ per mole of primary OH groups. After the feeding in of the $SO_3$ has been stopped, the reaction mixture is kept for a further hour at 25° C. while stirring, then 24.8 g of a 30% by weight aqueous sodium hydroxide solution which was diluted with 50 cm$^3$ of tri-n-propylamine is added to the reaction mixture and working up is carried out as described in Example 1. A bright odorless cohesive crystalline mass is obtained which contains 31% by weight of sodium salt of the sulfated diglycerol monolaurate and 6.8% by weight of sodium sulfate.

We claim:

1. A process for the sulfation of primary free OH-groups of partial esters obtained by esterifying polyhydric alcohols with aliphatic carboxylic acids containing 1 to 25 carbon atoms or with arylaliphatic acids containing 7 to 16 carbon atoms, comprising:

reacting said partial esters with $SO_3$ in the presence of a solvent at a reaction temperature in the range of about 0 to 60° C., said solvent being liquid under the reaction conditions and comprising at least one nitrogen-containing compound, said nitrogen-containing compound having a boiling point of 40° to 200° C. at a pressure of 98 kPa and having at least one trivalent nitrogen atoms which is linked to three carbon atoms and, besides said trivalent nitrogen atoms, contains only carbon and hydrogen atoms or carbon, hydrogen, and ether oxygen atoms, said nitrogen-containing compound being present in such an amount that the entire partial ester of the aliphatic polydric alcohol goes into solutions at the reaction temperature.

2. The process as claimed in claim 1, wherein 0.9 to 1.2 mol of $SO_3$ are used per 1 mol of primary free OH group of the partial ester.

3. The process as claimed in claim 1, wherein the $SO_3$ is used in gaseous form mixed with an inert gas, this mixture containing 1 to 30% by volume of $SO_3$.

4. The process as claimed in claim 1, wherein, after stopping the addition of $SO_3$ an alkali hydroxide or alkaline earth hydroxide is added to the reaction mixture and the solvent is then distilled off.

5. The process s claimed in claim 4, wherein 1 to 1.4 equivalents of the alkali hydroxide or alkaline earth hydroxide are used per 1 mol of $SO_3$ employed.

6. The process as claimed in claim 1, wherein at least one carboxylic acid monoester of glycerol, diglycerol, ethylene glycol or diethylene glycol is used as partial ester.

7. The process as claimed in claim 1, wherein at least one compound is used as solvent which has a boiling point of 60° to 150° C. at a pressure of 98 kPa.

8. The process as claimed in claim 4, wherein the alkali hydroxide or alkaline earth hydroxide is added after a post-reaction time.

9. The process as claimed in claim 1, wherein, after stopping the addition of $SO_3$, the amine salt of the sulfated partial ester of the aliphatic polyhydric alcohol which has resulted from the reaction of said partial ester with $SO_3$ in the presence of said solvent is recovered as the product of the reaction.

10. The process as claimed in claim 1, wherein the said partial ester is dissolved in a solvent consisting essentially of a said nitrogen-containing compound, and the resulting solution is brought into contact with $SO_3$.

* * * * *